(12) United States Patent
Fukuda et al.

(10) Patent No.: US 8,252,583 B2
(45) Date of Patent: Aug. 28, 2012

(54) METHOD FOR INDUCING DIFFERENTIATION INTO CARDIOMYOCYTES USING G-CSF

(75) Inventors: Keiichi Fukuda, Nerima-ku (JP); Shinsuke Yuasa, Shinjuku-ku (JP); Kenichiro Shimoji, Utsunomiya (JP)

(73) Assignee: Keiichi Fukuda, Tokyo (JP)

( * ) Notice: Subject to any disclaimer, the term of this patent is extended or adjusted under 35 U.S.C. 154(b) by 0 days.

(21) Appl. No.: 12/663,464

(22) PCT Filed: Jun. 6, 2008

(86) PCT No.: PCT/JP2008/060808
§ 371 (c)(1),
(2), (4) Date: Jun. 14, 2010

(87) PCT Pub. No.: WO2008/150030
PCT Pub. Date: Dec. 11, 2008

(65) Prior Publication Data
US 2011/0129922 A1 Jun. 2, 2011

(30) Foreign Application Priority Data
Jun. 7, 2007 (JP) .................... 2007-151170

(51) Int. Cl.
*C12N 5/00* (2006.01)
*C12N 5/02* (2006.01)
*C12N 5/07* (2010.01)
*C12N 5/071* (2010.01)

(52) U.S. Cl. ........ 435/325; 435/385; 435/363; 435/366; 435/373; 435/377; 435/395

(58) Field of Classification Search .................... 435/477
See application file for complete search history.

(56) References Cited

U.S. PATENT DOCUMENTS

| 5,843,780 | A | 12/1998 | Thomson |
| 6,015,671 | A | 1/2000 | Field |
| 6,090,622 | A | 7/2000 | Gearhart et al. |
| 2006/0051318 | A1 | 3/2006 | Fujiwara et al. |
| 2007/0134215 | A1 | 6/2007 | Fukuda et al. |

FOREIGN PATENT DOCUMENTS
WO 03006950 A2 1/2003

OTHER PUBLICATIONS

Yuasa et al. Transient inhibition of BMP signaling by Noggin induces cardiomyocyte differentiation of mouse embryonic stem cells, Nature Biotech, v 23 No. 5, pp. 607-611, 2005.*
Shimoji et al. G-CSF Promotes the Proliferation of Developing Cardiomyocytes In Vivo and in Derivation from ESCs and iPSCs. Cell Stem Cell vol. 6 pp. 227-237, 2010.*
Fukuhara et al. G-CSF Promotes Bone Marrow Cells to Migrate Into Infarcted Mice Heart and Differentiate Into Cardiomyocytes. Cell Transplantation, vol. 13, pp. 741-748, 2004.*
Soonpaa et al., "Formation of nascent intercalated disks between grafted fetal cardiomyocytes and host myocardium," Science, 1994, pp. 98-101, vol. 264.
Maltsev et al.,"Embryonic stem cells differentiate in vitro into cardiomyocyted representing sinusnodal, atrial and ventricular cell types," Mechanisms of Development, 1993, pp. 41-50, vol. 44.
Maltsev et al.,"Cardiomyocytes differentiated in vitro from embryonic stem cells developmentally express cardiac-specific genes and ionic currents," Circulation research, 1994, pp. 233-244, vol. 75, No. 2.
Klug et al.,"Genetically selected cardiomyocytes from differentiating embryonic stem cells form stable intracardiac grafts," J. Clin. Invest., 1996, pp. 216-224, vol. 98, No. 1.
Thomson et al,"Isolation of a primate embryonic stem cell line," PNAS, 1995, pp. 7844-7848, vol. 92.
Thomson et al., "Embryonic stem cell lines derived from human blastocysts," Science, 1998, retrieved from www.sciencemag.org, pp. 1145-1147, vol. 282.
Shamblott et al.,"Derivation of pluripotent stem cells from cultured human primordial germ cells," PNAS, 1998, pp. 13726-13731, vol. 95.
Chunhui et al.,"Characterization and enrichment of cardiomyocytes derived from human embryonic stem cells," Circulation research, 2002, pp. 501-508, vol. 91.
Wobus et al.,"Retinoic acid accelerates embryonic stem cell-derived cardiac differentiation and enhances development of ventricular cardiomyocytes," Journal of Molecular and Cellular Cardiology, 1997, pp. 1525-1539, vol. 29.
Takahashi et al.,"Ascorbic acid enhances differentiation of embryonic stem cells into cardiac myocytes." Circulation, 2003, pp. 1912-1916, Dallas, TX, USA.
Behfar et al.,"Stem cell differentiation requires a paracrine pathway in the heart," The FASEB journal, 2002, pp. 1558-1566, vol. 16.
Sachinidis et al.,"Cardiac specific differentiation of mouse embryonic stem cells," Cardiovascular research, 2003, pp. 278-291, vol. 58.
Ventura et al.,"Dynorphin B is an agonist of nuclear opioid receptors coupling nuclear protein kinase C activation to the transcription of cardiogenic genes in GTR1 embryonic stem cells," Circulation research, 2003, pp. 623-629, Dallas, TX, USA.
Sauer at al.,"Role of reactive oxygen species and phosphatidylinositol 3-kinase in cardiomyocyte dirrerentiation of embryonic stem cells," FEBS Letter, 2000, pp. 218-223, vol. 476.
Li et al.,"Calreticulin reveals a critical Ca2+ checkpoint in cardiac myofibrillogenesis," The Journal of Cell Biology, 2002, pp. 103-113, vol. 158, No. 1, Rockefeller University Press.
Minatoguchi et al.,"Acceleration of the healing process and myocardial regeneration may be important as a mechanism of improvement of cardiac function and remodeling by postinfarction granulocyte colony-stimulating factor treatment," Circulation, 2004, pp. 2572-2580, vol. 109, Dallas, TX, USA.

(Continued)

*Primary Examiner* — Celine Qian
*Assistant Examiner* — Addison D Ault
(74) *Attorney, Agent, or Firm* — Browdy and Neimark, PPLC

(57) ABSTRACT

A method for inducing differentiation of ES cells into cardiomyocytes, which comprises contacting the ES cells with an agonist for G-CSF receptor.

11 Claims, 14 Drawing Sheets

OTHER PUBLICATIONS

International Search Report issued in PCT/JP2008/060808.

Cho et al., "Granulocyte colony-stimulating factor treatment enhances the efficacy of cellular cardiomyoplasty with transplantation of embryonic stem cell-derived cardiomyocytes in infarcted myocardium," Biochemical and Biophysical Research Communications 340(2): 573-582 (Feb. 10, 2006).

Umeda et al., "Development of primitive and definitive hematopoiesis from nonhuman primate embryonic stem cells in vitro", Development 131(8): 1869-1879 (Jan. 8, 2004).

Otsuka et al., "Kotsuzui Saibo no Shinkin Saibo eno Bunka Yudo", Experimental Medicine, 2003 21(8): 106-110 (2003).

Kehat et al.,"Human embryonic stem cells can differentiate into myocytes with structural and functional properties of cardiomyocytes," J. Clin. Invest., 2001, pp. 407-414, vol. 108, No. 3.

Xu et al., Characterization and enrichment of cardiomyocytes derived from human embryonic stem cells, Circ. Res., 2002, pp. 501-508, vol. 91, No. 6.

\* cited by examiner

Administered with BrdU at embryonic day 10.5 and analyzed at embryonic day 12.5

METHOD FOR INDUCING DIFFERENTIATION INTO CARDIOMYOCYTES USING G-CSF

TECHNICAL FIELD

The present invention provides a method for inducing differentiation of ES cells into cardiomyocytes, and cardiomyocytes obtainable by this method, as well as an inducer of cardiomyocyte differentiation, etc.

BACKGROUND ART

Cardiomyocytes undergo active cell division with beating autonomously before birth, but immediately after birth they lose the ability to divide, and since they have little undifferentiated progenitor cells, when cardiomyocytes die due to exposure to various forms of stress including myocardial infarction, myocarditis and the like, the lost cardiomyocytes cannot be regenerated. As a result, the surviving cardiomyocytes try to maintain myocardial function through compensatory hypertrophy and the like, but if the stress continues and exceeds an allowable threshold, it leads to further exhaustion and death of cardiomyocytes and a consequent lowering of myocardial function (that is, heart failure).

Therefore, it would seem that methods of transplantation to replace weakened or lost cardiomyocytes would be extremely useful for the treatment of heart failure. In fact, it is known from animal experiments that when immature cardiomyocytes obtained from fetuses are transplanted into adult cardiac tissue, the transplanted cells function effectively as cardiomyocytes (See Non-Patent Document 1). However, it is difficult to obtain sufficient cardiomyocytes for this method, and application to clinical medicine is also difficult from an ethical standpoint.

Attention has therefore focused in recent years on inducing differentiation of stem cells into cardiomyocytes and using these cells for transplantation. At present it has not yet been possible to clearly identify a population of progenitor cells or stem cells capable of producing cardiomyocytes in adult cardiac tissue, so pluripotent stem cells, which are less differentiated and can differentiate into a variety of cells, are considered to be useful for the above method.

Pluripotent stem cells are defined as cells which are capable of indefinite or long-term cell proliferation while remaining in an undifferentiated state in an in vitro culture, which retain normal karyotypes, and which have the ability to differentiate into all of three germ layers (ectoderm, mesoderm and endoderm) under appropriate conditions. At present, the three well-known pluripotent stem cells are embryonic stem cells (ES cells) derived from early-stage embryos, embryonic germ cells (EG cells) derived from primordial germ cells at the embryonic stage, and multipotent adult progenitor cells (MAPC) isolated from adult hone marrow.

In particular, it has long been known that ES cells can be induced to differentiate into cardiomyocytes in vitro. Mouse ES cells were used in most of the early studies. When ES cells are cultured in suspension culture as single cells (individual cells dispersed with no adhesion between cells due to enzyme treatment or the like) without the presence of a differentiation-inhibiting factor such as leukemia inhibitory factor (LIF) or the like, the ES cells adhere to one another and aggregate, forming a structure called embryoid bodies (EBs) which are similar to the early embryonal structures. It is also known that cardiomyocytes with spontaneous beating ability appear when these EBs are cultured in suspension or in adhesion on the surface of culture devices.

ES cell-derived cardiomyocytes prepared as described above exhibit very similar properties to those of immature cardiomyocytes in fetal hearts (See Non-Patent Documents 2 and 3). Moreover, it has been confirmed from animal experiments that when ES cell-derived cardiomyocytes are actually transplanted into adult cardiac tissues, they are highly effective, with results similar to those obtained by transplantation of fetal myocardium (See Patent Document 1; Non-Patent Document 4).

In 1995, Thomson et al. first established ES cells from primates (See Patent Document 2; Non-Patent Document 5), and thus the regeneration therapy using pluripotent stem cell-derived cardiomyocytes has become realistic. Subsequently they also succeeded in isolating and establishing human ES cell lines from early human embryos (See Non-Patent Document 6). Moreover, Gearhart et al. established human EG cell lines from human primordial germ cells (See Non-Patent Document 7; Patent Document 3).

Kehat et al. (See Non-Patent Document 8) and Chunhui et al. (See Patent Document 4; Non-Patent Document 9) have reported that human ES cells can differentiate into cardiomyocytes, as mouse ES cells can do. According to these reports, cardiomyocytes derived from human ES cells not only have the ability to beat spontaneously but also express and produce cardiomyocyte-specific proteins such as myosin heavy and light chains, α-actinin, troponin I and atrial natriuretic peptide (ANP) and cardiomyocyte-specific transcription factors such as GATA-4, Nkx2.5, MEF-2c and the like, and from microanatomical observation and electrophysiological analysis it appears that they retain the properties of immature cardiomyocytes at the fetal stage, and could be used for regenerative therapy.

However, one serious problem remains to be elucidated to use pluripotent stem cell-derived cardiomyocytes for cell transplantation therapy and other purposes. When EBs are formed from ES cells or EG cells by conventional methods, not only cardiomyocytes, but also other types of differentiated cells, such as blood cells, vascular cells, neural cells, intestinal cells, bone and cartilage cells and the like, are developed. Moreover, the proportion of cardiomyocytes in these differentiated cell population is not so high, only about 5% to 20% of the total.

Methods of isolating only cardiomyocytes from a mixture of various kinds of cells include a method of adding an artificial modification to the ES cell genes, conferring drug resistance or ectopic expression, and collecting cells having the properties of cardiomyocytes or progenitor cells thereof. For example, by introducing a gene cassette capable of expressing a neomycin (G418) resistance gene under the control of the α-myosin heavy chain promoter into mouse ES cells, Field and his co-researchers established a system in which those ES cells could only survive in medium to which G418 had been added when they differentiated into cardiomyocytes and expressed the α-myosin heavy chain gene (See Patent Document 1; Non-Patent Document 4). 99% or more of G418-resistant cells selected by this method were confirmed to be cardiomyocytes. However, although the purity of the cardiomyocytes is extremely high in this method, the final number of cardiomyocytes obtained is only a few percent of the total cell count, making it difficult to obtain enough amounts of cardiomyocytes for transplantation.

Recently, Chunhui et al. have reported that when human ES cells are treated with 5-azacytidine, the percentage of troponin I-positive cells (cardiomyocytes) in EBs rises from 15% to 44% (See Non-Patent Document 9), but even in this method the percentage of cardiomyocytes in EBs does not exceed 50%. Moreover, 5-azacytidine is a demethylation agent that alters the expression of genes by removing methyl groups bound to DNA, and because it acts directly on the chromosomes, it is not a suitable drug for preparing cells for cell transplantation.

Other methods for producing cardiomyocytes more efficiently from ES cells include, in the case of mouse ES cells, addition of retinoic acid (See Non-Patent Document 10), ascorbic acid (See Non-Patent Document 11), TGFβ, BMP-2 (See Non-Patent Document 12), PDGF (See Non-Patent Document 13) and Dynorphin B (See Non-Patent Document. 14) and treatment to increase reactive oxygen species (ROS) (See Non-Patent Document 15) and $Ca^{2+}$ (See Non-Patent Document 16) in the cells, all of which are known to act positively to induce cardiomyocyte differentiation. However, cardiomyocyte-specific or selective differentiation has not been achieved with any of these methods.

The inventors of the present invention have found that when a substance that inhibits bone morphogenic protein (BMP) signaling, particularly Noggin, is added to medium during a certain stage of culture, cells having beating ability which are identified as cardiomyocytes are produced with much higher selectivity and efficiency than in conventional methods (see Patent Document 5).

Granulocyte colony-stimulating factor (hereinafter referred to as G-CSF), which is a hematopoietic factor that was discovered as a differentiation-inducing factor for granulocyte lineage hematopoietic stem cells, is known to promote neutrophil hematopoiesis in the body and hence is clinically used as a therapeutic agent for neutropenia following bone marrow transplantation and/or cancer chemotherapy. In addition to these actions, human G-CSF is reported to act on stem cells to stimulate their differentiation and proliferation, and is also reported to induce recruitment of stem cells in the bone marrow into peripheral blood. It has been reported from in vivo experiments that bone marrow stem cells recruited by G-CSF differentiate into cardiomyocytes in tissue where they were recruited (Patent Document 6; Non-patent Document 17). However, there is no report showing that G-CSF directly induces bone marrow stem cells to differentiate into cardiomyocytes, and there is also no report showing that G-CSF is expressed in embryonic cardiomyocytes or is directly used to induce cardiomyocyte differentiation. Moreover, there is no report showing that G-CSF acts directly on ES cells and is used to induce their differentiation into cardiomyocytes.

As described above, conventional methods alone result in variations in the efficiency of myocardial induction, and there is a demand for a more efficient and selective method for inducing differentiation into cardiomyocytes.

Patent Document 1: U.S. Pat. No. 6,015,671
Patent Document 2: U.S. Pat. No. 5,843,780
Patent Document 3: U.S. Pat. No. 6,090,622
Patent Document 4: International Patent Publication No. WO03/06950
Patent Document 5: International Patent Publication No. WO05/033298
Patent Document 6: International Patent Publication No. WO04/054604
Non-patent Document 1: Soonpaa et al., Science, 264:98, 1994
Non-patent Document 2: Maltsev et al., Mech. Dev., 44:41, 1993
Non-patent Document 3: Maltsev et al., Circ. Res., 75:233, 1994
Non-patent Document 4: Klug et al., J. Clin. Invest., 98:216, 1996
Non-patent Document 5: Thomson et al., Proc. Natl. Acad. Sci. USA, 92:7844, 1995
Non-patent Document 6: Thomson et al., Science, 282: 114, 1998
Non-patent Document 7: Sha blott et al., Proc. Natl. Acad. Sci. USA, 95:13726,
Non-patent Document 8: Kehat et al., J. Clin. Invest., 108: 407, 2001
Non-patent Document 9: Chunhui et al., Circ. Res., 91:508, 2002
Non-patent Document 10: Wobus et al., J. Mol. Cell. Cardiol., 29:1525, 1997
Non-patent Document 11: Takahashi et al., Circulation, 107:1912, 2003
Non-patent Document 12: Behfar et al., FASEB J., 16:1558, 2002
Non-patent Document 13: Sachinidis et al., Cardiovasc. Res., 58:278, 2003
Non-patent Document 14: Ventura et al., Circ. Res., 92:623, 2003
Non-patent Document 15: Sauer et al., FEBS Lett., 476: 218, 2000
Non-patent Document 16: Li et al., J. Cell Biol., 158:103, 2002
Non-patent Document 17: Minatoguchi et al., Circulation, 109:2572, 2004

DISCLOSURE OF THE INVENTION

Problems to be Solved by the Invention

The present invention aims to provide a method for efficiently and selectively inducing cardiomyocyte differentiation from undifferentiated ES cells, cardiomyocytes obtainable by this method, and an inducer of cardiomyocyte differentiation, etc.

Means for Solving the Problems

The inventors of the present invention have found that G-CSF receptor is strongly expressed in mouse embryonic cardiomyocytes, and that G-CSF is involved in proliferation of embryonic cardiomyocytes. As a result of repeating various studies on ES cells to examine the conditions for inducing their differentiation into cardiomyocytes, the inventors have further found that cells having heating ability which are identified as cardiomyocytes are produced upon addition of an agonist for G-CSF receptor to medium during a certain stage of culture, and that G-CSF has a strong proliferative activity on cardiomyocytes during differentiation from ES cells into cardiomyocytes. These findings led to the completion of the present invention.

Namely, the present invention provides the following.
(1) A method for inducing differentiation of ES cells into cardiomyocytes, which comprises contacting the ES cells with an agonist for G-CSF receptor.
(2) The method according to (1) above, which comprises culturing the ES cells in the presence of the agonist for G-CSF receptor.
(3) The method according to (1) or (2) above, wherein the agonist for G-CSF receptor is G-CSF.
(4) The method according to any one of (1) to (3) above, which comprises the following steps:
  (a) adding G-CSF to a cell culture solution; and
  (b) culturing the ES cells using the culture solution from step (a).

(5) The method according to any one of (1) to (4) above, wherein the ES cells and G-CSF are contacted in vitro.

(6) The method according to any one of (1) to (5) above, which further comprises the step of culturing the ES cells in the presence of a substance that inhibits BMP signaling, prior to contacting the ES cells with the agonist for G-CSF receptor.

(7) The method according to (6) above, wherein the substance that inhibits BMP signaling is Noggin.

(8) Cardiomyocytes obtainable by the method according to any one of (1) to (7) above.

(9) An inducer of cardiomyocyte differentiation from ES cells, which comprises an agonist for G-CSF receptor.

(10) The inducer of cardiomyocyte differentiation according to (9) above, wherein the agonist for G-CSF receptor is G-CSF.

(11) The inducer of cardiomyocyte differentiation according to (9) or (10) above, which is used in vitro.

(12) Use of an agonist for G-CSF receptor to induce differentiation of ES cells into cardiomyocytes.

(13) The use according to (12) above, wherein the agonist for G-CSF receptor is G-CSF.

(14) The use according to (12) or (13) above, which is used in vitro.

It should be noted that anyone implementing the present invention can consult standard references regarding ordinary methods of cell culture and developmental and cytobiological experiments using ES cells. These include Guide to Techniques in Mouse Development (Wasserman et al., eds., Academic Press, 1993); Embryonic Stem Cell Differentiation in vitro (M. V. Wiles, Meth. Enzymol. 225:900, 1993); Manipulating the Mouse Embryo: A laboratory manual (Hogan et al., eds., Cold Spring Harbor Laboratory Press, 1994); and Embryonic Stem Cells (Turksen ed., Humana Press, 2002). The reagents and kits for cell culture and developmental and cytobiological experiments cited herein can be obtained from commercial sources including Invitrogen/GIBCO, Sigma and the like.

BRIEF DESCRIPTION OF THE DRAWINGS

FIG. 5a presents photographs of the same heart sections as in FIG. 4, which are stained with hematoxylin-eosin and observed under a microscope. FIG. 5b presents photographs of heart sections from G-CSFR knockout and wild-type mice, which are stained with hematoxylin-eosin and observed under a microscope. In the figure, LV denotes left ventricle, RV denotes right ventricle, LA denotes left atrium, and RA denotes right atrium.

FIG. 21a shows the results observed for spontaneous beating in common marmoset ES (CMES) cells. FIG. 21b presents photographs showing the results of RT-PCR analysis for the expression of various cardiomyocyte markers in CMES cells treated with mouse G-CSF or human G-CSF. FIG. 21c presents photographs showing the results of immunostaining analysis for the expression of cardiac troponin I and Nkx2.5 in CMES-derived EBs in the G-CSF-treated and untreated groups.

BEST MODE FOR CARRYING OUT THE INVENTION

Figure 1:
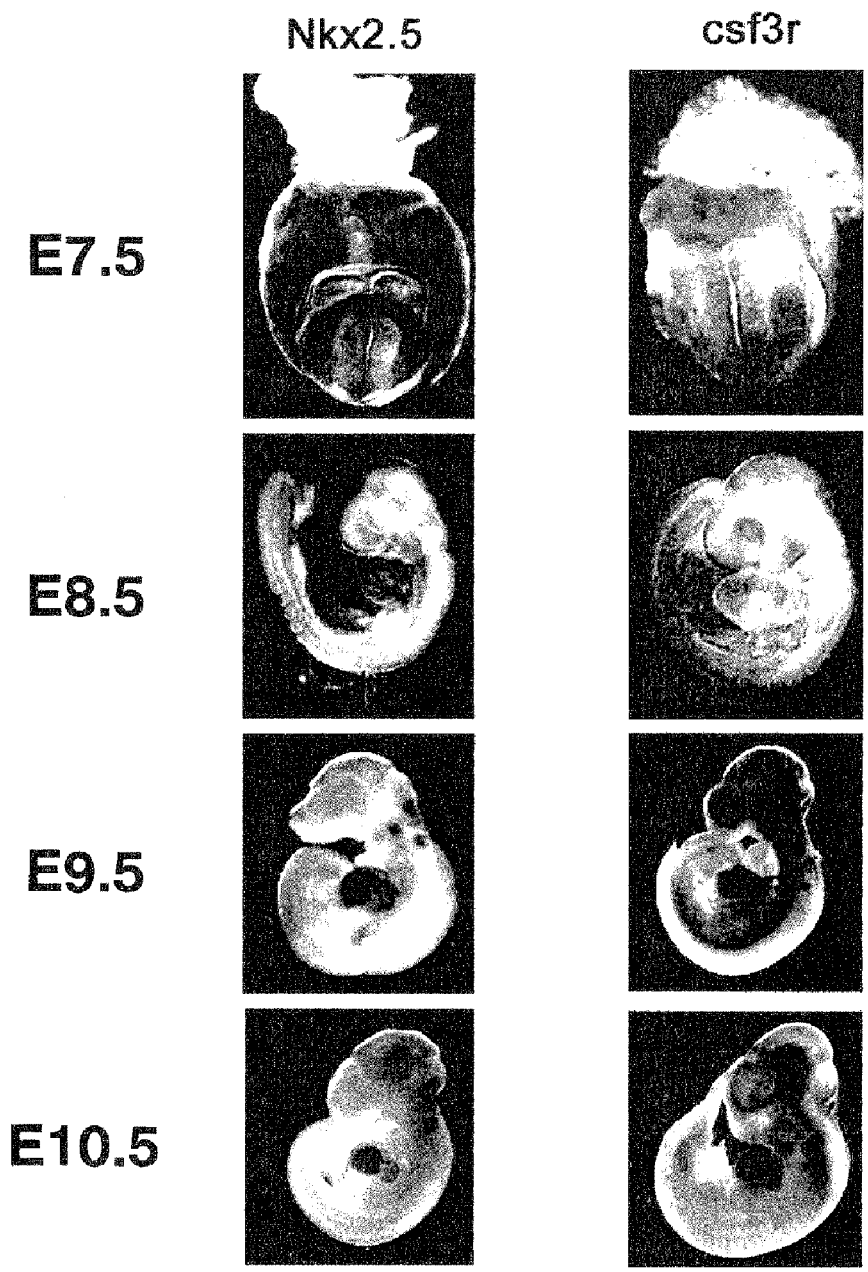
FIG. 1 presents photographs of in situ hybridization showing the expression of mouse G-CSF receptor (csf3r) and cardiomyocyte-specific transcription factor Nkx2.5 in fetal mouse hearts.

ES cells used in the present invention include ES cells of mammalian origin (e.g., mouse, monkey, human), which are already widely used as cultured cell lines. Specific examples of mouse ES cells include EB3 cells, E14 cells, D3 cells, CCE cells, R1 cells, 129SV cells, J1 cells and so on. Specific examples of monkey ES cells include common marmoset ES cells. Standard protocols have been established for preparing, subculturing and preserving ES cells, and in addition to the references cited above, the operator can easily use these ES cells by consulting various other references (Matsui et al., Cell 70:841, 1992; Shamblott et al., Proc. Natl. Acad. Sci, USA 95:13726, 1998; U.S. Pat. No. 6,090,622; Jiang et al., Nature 418:41, 2002; International Patent Publication No. WO01/11011).

In the present invention, "cardiomyocytes" include cardiomyocyte progenitor cells having the ability to become functional cardiomyocytes in the future, as well as fetal and adult cardiomyocytes at all stages of differentiation, and refer to cells that can be identified by one or preferably more than one of the following methods using one or preferably more than one marker or index.

The expression of various markers specific to cardiomyocytes is detected by conventional biochemical or immunochemical methods. There is no particular limit on the method, but preferably an immunochemical method such as immunohistochemical staining or immunoelectrophoresis is used. In these methods, marker-specific polyclonal antibodies or monoclonal antibodies can be used which react with cardiomyocyte progenitor cells or cardiomyocytes. Antibodies for individual specific markers are commercially available, and can be easily used. Markers specific to cardiomyocyte progenitor cells or cardiomyocytes include for example myosin heavy and light chains, α-actinin, troponin 1, ANP, GATA-4, Nkx2.5, MEF-2c and the like.

Alternatively, although the method is not particularly limited, expression of cardiomyocyte progenitor cell-specific or cardiomyocyte-specific marker genes can also be confirmed by molecular biological methods, such as reverse transcriptase polymerase chain reaction (RT-PCR) and hybridization analysis, which have been commonly used in the past for amplifying, detecting and analyzing mRNA encoding any marker proteins. The nucleic acid sequences encoding marker proteins specific to cardiomyocyte progenitor cells and cardiomyocytes (such as myosin heavy and light chains, α-actinin, troponin I, ANP, GATA-4, Nkx2.5 and MEF-2c) are already known and are available through public databases such as GenBank, and the marker-specific sequences needed for use as primers or probes can be easily determined.

Physiological indexes can also be used additionally to confirm differentiation of ES cells into cardiomyocytes. For example, useful markers include the ability of cells derived from ES cells to beat spontaneously, and the ability of cells derived from ES cells to react to electrophysiological stimulus through various ion channels expressed on the cells.

The "agonist for G-CSF receptor" intended in the present invention is not limited in any way as long as it can bind to G-CSF receptor and thereby induce G-CSF receptor signaling. Such an agonist for G-CSF receptor is any substance including a peptide, an agonist antibody, a low-molecular compound, etc. The amino acid sequence of G-CSF receptor is known (International Publication No. WO91/14776).

G-CSF can be presented as a preferred example of the agonist for G-CSF receptor. G-CSF used in the present invention can be any G-CSF, but preferably highly purified G-CSF, more specifically mammalian G-CSF, especially having biological activity substantially identical to that of human G-CSF. G-CSF may be of any origin, and it is possible to use naturally derived G-CSF, recombinantly obtained G-CSF or the like, but preferred is recombinantly obtained G-CSF. Recombinantly obtained G-CSF may have an amino acid sequence identical to that of naturally derived G-CSF or may contain a deletion, substitution, addition or other modification of one or more amino acids in the amino acid sequence so far as it has similar biological activity to that of naturally derived G-CSF. The amino acid sequence of naturally derived G-CSF is known (SEQ ID NO: 1). Amino acid deletion, substitution, addition or other modification can be performed by methods known to those skilled in the art. For example, a polypeptide functionally comparable to G-CSF can be prepared by those skilled in the art by introducing an amino acid variation into G-CSF as appropriate via site-directed mutagenesis (Gotoh, T. et al. (1995) Gene 152, 271-275; Zoller, M. J. and Smith, M. (1983) Methods Enzymol. 100, 468-500; Kramer, W. et al. (1984) Nucleic Acids Res. 12, 9441-9456; Kramer, W. and Fritz, H. J. (1987) Methods Enzymol. 154, 350-367; Kunkel, T. A. (1985) Proc. Natl. Acad. Sci. USA. 82, 488-492; Kunkel (1988) Methods Enzymol. 85, 2763-2766) or other techniques. Amino acid variations also occur in nature. The number of amino acids to be substituted, deleted or added is not limited in any way, but it is preferably 30 amino acids or less, more preferably 20 amino acids or less, and even more preferably 10 amino acids or less (e.g., 5 amino acids or less). Moreover, a polypeptide functionally comparable to G-CSF generally shares high homology with the amino acid sequence of SEQ ID NO: 1. In the present invention, high homology is intended to mean 70% or more homology, preferably 80% or more homology, even more preferably 90% or more homology, and still even more preferably 95% or more homology with the amino acid sequence of SEQ ID NO: 1. Amino acid homology may be determined, for example, according to the reported algorithm (Wilbur, W. J. and Lipman, D. J. Proc. Natl. Acad. Sci. USA (1983) 80, 726-730). Generally, an amino acid residue is preferably substituted by another amino acid residue in which the property of the amino acid side chain is conserved. For example, the properties of amino acid side chains include hydrophobic amino acids (A, I, L, M, F, P, W, Y, V), hydrophilic amino acids (R, D, N, C, E, Q, G, H, K, S, T), amino acids having aliphatic side chains (G, A, V, L, I, P), amino acids having hydroxyl-containing side chains (S, T, Y), amino acids having sulfur-containing side chains (C, M), amino acids having carboxylate- and amide-containing side chains (D, N, E, Q), amino acids having base-containing side chains (R, K, H), and amino acids having aromatic-containing side chains (H, F, Y, W) (examples shown by one-letter amino acid codes within parentheses). It has been already known that polypeptides having an amino acid sequence modified by deleting, adding and/or substituting one or more amino acid residues retain their biological activity (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

Fusion proteins of G-CSF and another protein can also be used. Fusion proteins can be prepared by, e.g., ligating the DNA encoding G-CSF in-frame with the DNA encoding another protein, inserting the ligation product into an expression vector and expressing it in a host. The second protein to be fused to G-CSF in the present invention is not specifically limited.

Chemically modified G-CSF can also be used. Examples of chemically modified G-CSF include, for example, G-CSF subjected to conformational change, addition or deletion of the sugar chain, as well as G-CSF conjugated to a compound such as an inorganic or organic compound, e.g., polyethylene glycol, vitamin B12, etc.

It is also possible to use a partial peptide of G-CSF. Such a partial peptide of G-CSF is not limited in any way, but it generally has binding activity to G-CSF receptor.

G-CSF used in the present invention may be produced in any manner. For example, it is possible to use G-CSF obtained by culturing a human tumor cell line or a human G-CSF-producing hybridoma cell line, followed by extraction, isolation and purification in various manners, or G-CSF obtained by being produced in E. coli cells, yeast cells, Chinese hamster ovary cells (CHO cells), C127 cells, COS cells, myeloma cells, BHK cells, insect cells or other cells by genetic engineering procedures, followed by extraction, isolation and purification in various manners. G-CSF used in the present invention is preferably G-CSF produced by genetic engineering procedures, preferably using mammalian cells (particularly CHO cells) (see, e.g., JP H01-44200 B, JP H02-5395 B, JP S62-129298 A, JP S62-132899 A, JP S62-236488 A, JP S64-85098 A).

As described later in the Example section, the inventors of the present invention have found that G-CSF receptor is strongly expressed in mouse embryonic cardiomyocytes, and that G-CSF is involved in proliferation of embryonic cardiomyocytes. In addition, the inventors have confirmed, ahead of others, that G-CSF remarkably promotes in vivo proliferation of cardiomyocytes at the embryonic stage. Further, in the present invention, G-CSF is found to be essential for primate cardiomyocyte proliferation, thus suggesting the role of G-CSF in all mammals, including humans.

Any method suited to inducing differentiation of cardiomyocytes can be used as the culture method for preparing cardiomyocytes from ES cells in the present invention, and examples include floating aggregate culture, hanging drop culture, co-culture with supporting cells, gyratory culture, soft agar culture, micro-carrier culture and the like. In the case of floating aggregate culture for example, a specific example is a method of suspending ES cells as single cells (individual cells dispersed in a liquid phase with no adhesion between cells due to enzyme digestion or the like) in medium to a cell density of preferably 10 cells/mL to $1\times10^7$ cells/mL, more preferably 100 cells/mL to $1\times10^6$ cells/mL, seeding them on a culture plate, and culturing them for 4 to 30 days, preferably 6 to 15 days at 37° C. under $CO_2$ conditions of 5% carbon dioxide ventilation.

In a different embodiment using a co-culture method with supporting cells, the supporting cells are not particularly limited but are preferably cells having the characteristics of mesenchymal cells and more preferably cells having bone marrow stroma cell-like properties, such as ST2 cells, OP9 cells, PA6 cells or the like. These supporting cells are cultured to a high density and made into a feeder by a method such as mitomycin C treatment, irradiation or the like, and ES cells suspended as single cells in medium to a cell density of 1 cell/mL to $1\times10^6$ cells/mL, preferably 100 cells/mL to $1\times10^5$ cells/mL, more preferably $1\times10^3$ cells/mL to $1\times10^4$ cells/mL are seeded thereon and cultured for 4 to 30 days, preferably 6 to 15 days at 37° C. under $CO_2$ conditions of 5% carbon dioxide ventilation.

In the present invention, ES cells are contacted with an agonist for G-CSF receptor, preferably G-CSF, to thereby induce differentiation of the ES cells into cardiomyocytes. A preferred method for this purpose is to add purified recombinant G-CSF to medium. Any other methods may also be used as long as they produce the same effect as in the case of adding purified recombinant G-CSF to medium. Examples include a method in which a gene expression vector for G-CSF is introduced into ES cells per se, a method in which a gene expression vector for G-CSF is introduced into supporting cells and these transgenic cells are used as co-culture cells, or a method in which a cell product (e.g., culture supernatant) of such transgenic cells is used, each of which methods is encompassed in the method of the present invention as an embodiment for adding an agonist for G-CSF receptor to medium.

More specifically, for example, the present invention comprises the following steps:
  (a) adding G-CSF to a cell culture solution; and
  (b) culturing the ES cells using the culture solution from step (a).

In implementing the present invention, the agonist for G-CSF receptor to be used is preferably derived from the same animal species as that of ES cells, but an agonist derived from a different animal species may also be used.

In the present invention, ES cells and G-CSF are preferably contacted in vitro.

In implementing the present invention, to maintain ES cells in an undifferentiated state, the ES cells are preferably cultured under conditions commonly used as appropriate for their animal species. Namely, in the case of mouse ES cells, medium is preferably supplemented with leukemia inhibitory factor (LIF) at a concentration of 100 to 10000 U/mL, preferably 500 to 2000 U/mL.

The ES cells are then induced to differentiate into cardiomyocytes in LIF-free differentiation medium. In the initiation of differentiation induction, the ES cells are preferably cultured in the presence of a substance that inhibits BMP signaling, prior to contacting the ES cells with the agonist for G-CSF receptor. In the case of using a BMP antagonist (e.g., Noggin protein, Chordin protein) as a substance that inhibits BMP signaling, the medium is sterilely removed and replaced with fresh medium containing the Noggin or Chordin protein at a concentration of 1 ng/mL to 2 µg/ml, preferably 5 ng/mL to 1000 ng/mL, more preferably 10 ng/mL to 500 ng/mL, and culture is continued preferably for several days, more preferably for 3 days.

Subsequently, in the case of using G-CSF as an agonist for G-CSF receptor, the medium is sterilely removed and G-CSF is added at a final concentration in the medium of 0.01 ng/mL to 500 ng/ml, preferably 0.05 ng/mL to 300 ng/mL, more preferably 0.75 ng/mL to 25 ng/mL or 2.5 ng/mL to 25 ng/mL, and culture is continued. The timing of G-CSF addition is 3 to 10 days, more preferably 5 to 8 days after initiation of differentiation, although the optimum concentration and the time period of treatment may be varied as appropriate.

Cardiomyocytes derived from ES cells by the aforementioned method can be further collected, isolated and purified by known methods to efficiently obtain large quantities of highly pure cardiomyocytes.

Any known method of cell isolation and purification can be used as the method of purifying the cardiomyocytes, and specific examples include flow cytometry, magnetic beads, panning and other methods involving antigen-antibody reactions (Monoclonal Antibodies: principles and practice, Third Edition (Acad. Press, 1993); Antibody Engineering: A Practical Approach (IRL Press at Oxford University Press. 1996)) as well as cell fractioning by density gradient centrifugation using a carrier such as sucrose, Percoll or the like. Another method of selecting cardiomyocytes is to first artificially introduce a modification into the genes of the ES cells or other pluripotent stem cells, making them drug resistant or capable of ectopic protein expression, and collecting cells having the morphology of cardiomyocytes. For example, by introducing a gene cassette capable of expressing a neomycin (G418) resistance gene under the control of the α-myosin heavy chain promoter into mouse ES cells, Field and his co-researchers succeeded in constructing a system in which ES cells were differentiated into cardiomyocytes and only those cells which expressed the α-myosin heavy chain gene could survive in medium to which G418 had been added, and 99% or more of the cells selected as G418-resistant cells by this method were confirmed to be cardiomyocytes (U.S. Pat. No. 6,015,671; J. Clin. Invest. 98: 216, 1996).

In another embodiment, the present invention relates to cardiomyocytes prepared by inducing differentiation of ES cells using the above differentiation induction method of the present invention, i.e., cells which exhibit the morphological, physiological and/or immunological characteristics of cardiomyocytes. In terms of physiological and/or immunological properties, cells prepared by the method of the present invention may express one or more markers specific to cardiomyocytes which are recognized as cardiomyocytes, but this is not a limitation.

In yet another embodiment, the present invention relates to an inducer of cardiomyocyte differentiation from ES cells, which comprises an agonist for G-CSF receptor. A preferred agonist for G-CSF receptor is G-CSF, which is preferably used in vitro.

In yet another embodiment, the present invention relates to the use of an agonist for G-CSF receptor to induce differentiation of ES cells into cardiomyocytes. A preferred agonist for G-CSF receptor is G-CSF, which is preferably used in vitro.

Cardiomyocytes prepared according to the present invention can be used as myocardial regeneration drugs or heart disease treatment drugs. Examples of heart disease include myocardial infarction, ischemic heart disease, congestive heart failure, hypertrophic cardiomyopathy, dilative cardiomyopathy, myocarditis, chronic heart failure and the like. When used as myocardial regeneration drugs or heart disease treatment drugs, cardiomyocytes prepared according to the present invention can be included in any form as long as the purity is high, such as cells suspended in the medium or other aqueous carrier, cells embedded in a biodegradable substrate or other support, or cells made into a single-layer or multi-layer myocardial sheet (Shimizu et al., Circ. Res. 90:e40, 2002).

Although not particularly limited to these, methods for transporting the aforementioned therapeutic drug to a damage site include direct injection into the heart via an open chest and a syringe, methods of transplantation via a surgical incision in the heart, and methods of transplantation via the blood vessels using a catheter (Murry et al., Cold Spring Harb. Symp. Quant. Biol. 67:519, 2002; Menasche, Ann. Thorac. Surg. 75:S20, 2003; Dowell et al., Cardiovasc. Res. 58:336, 2003). Extremely good therapeutic effects have been reported when cardiomyocytes collected from a fetal heart were transplanted by such methods to the hearts of animals with heart damage (Menasche, Ann. Thorac. Surg. 75:S20, 2003; Reffelmann et al., Heart Fail. Rev. 8:201, 2003). Cardiomyocytes derived from ES cells have characteristics extremely similar to those of cardiomyocytes derived from fetal hearts (Maltsev et al., Mech. Dev. 44:41, 1993; Circ. Res. 75:233, 1994). Moreover, an extremely high take rate equivalent to that achieved with fetal myocardial transplantation has been confirmed in animal experiments in which cardiomyocytes derived from ES cells were actually transplanted into adult hearts (King et al., J. Clin. Invest. 98:216, 1996). Consequently, it is expected that supplementary transplantation of cardiomyocytes prepared according to the present invention into diseased heart tissue should stimulate improved heart functions in cases of the aforementioned heart diseases stemming from damage or loss of heart cells.

Advantages of the Invention

The method of the present invention enables the efficient and selective production of cardiomyocytes from ES cells. In particular, the method of the present invention allows a higher induction efficiency when combined with the existing method(s) because the method of the present invention acts on myocardium immediately after differentiation. The cardiomyocytes thus prepared can be used for search and development of drugs effective for treatment of heart diseases, and also have the possibility of being applicable to myocardial transplantation for serious heart diseases.

EXAMPLES

The present invention will be further described in more detail by way of the following examples, which are provided for illustrative purposes only and are not intended to limit the scope of the invention.

Example 1

Expression of G-CSF Receptor in Fetal Mouse Heart-Derived Myocardium

The following procedures were used to study the expression of G-CSF receptor in fetal mouse heart-derived myocardium.

(1) Study by In Situ Hybridization

Pregnant ICR wild-type mice were purchased from CLEA Japan. At embryonic days E7.5, E8.5, E9.5 and E10.5, fetuses were collected and their hearts were analyzed by whole-mount in situ hybridization (WISH) using a digoxigenin-labeled RNA probe according to the reported method (Sasaki H. et al., Development 118, 47-59 (1993)). The full-length cDNAs of mouse G-CSF receptor (csf3r) and cardiomyocyte-specific transcription factor Nkx2.5 (whose accession numbers are NM_008711 and NM_008700, respectively) were obtained by reverse transcriptase PCR(RT-PCR) and each was subcloned into pBluescript plasmid. For csf3r, the sense primer used was 5'-CCC CTC AAA CCT ATC CTG CCT C-3' (SEQ ID NO: 2) and the antisense primer used was 5'-TCC AGG CAG AGA TCA GCG AAT G-3' (SEQ ID NO: 3). Likewise, for Nkx2.5, the sense primer used was 5'-CAG TGG AGC TGG ACA AAG CC-3' (SEQ ID NO: 4) and the antisense primer used was 5'-TAG CGA CGG TTC TGG AAC CA-3' (SEQ ID NO: 5). The probe was transcribed with T3 or T7 RNA polymerase. The results obtained are shown in FIG. 1. G-CSF receptor (csf3r) was strongly expressed at E7.5 and E8.5, but were not detected at the subsequent stages. In contrast, Nkx2.5 were expressed at later stages.

(2) Study by Immunostaining

Figure 2:
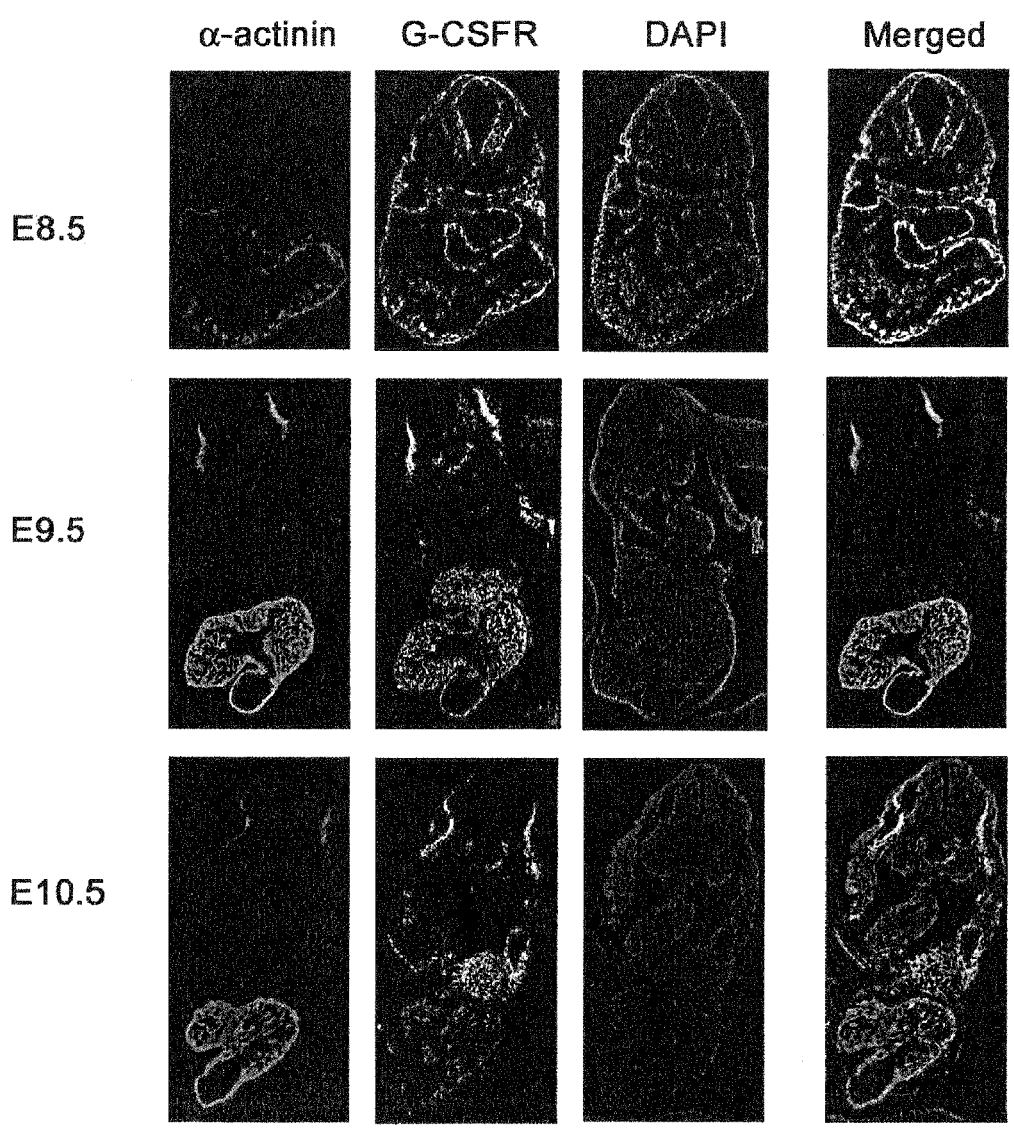
FIG. 2 presents photographs of immunostaining showing the expression of G-CSF receptor (G-CSFR) or cardiomyocyte-specific protein α-actinin in fetal mouse heart sections. Nucleic acids were stained with DAPI (4',6-diamidine-2-phenylindole dihydrochloride: Sigma Aldrich).

Mouse hearts at E8.5, E9.5 and E10.5 were fixed in 4% paraformaldehyde for 45 minutes and embedded using Tissue-Tek OCT (Sakura Finetek) to prepare sections. Each sample was bound to a primary antibody against G-CSF receptor (G-CSFR) (H176: santa cruz) or cardiomyocyte-specific protein α-actinin, further reacted with an Alexa488-labeled secondary antibody (Molecular Probes) and then observed under a fluorescent microscope. Nucleic acids were stained with DAP1 (4',6-diamidine-2-phenylindole dihydrochloride: Sigma Aldrich). The results obtained are shown in FIG. 2. It was continued that G-CSF receptor expression in the heart and somite started from embryonic day 8.5 and then reached a peak at embryonic day 9.5.

(3) Study by Reverse Transcriptase PCR(RT-PCR) Reaction

Figure 3:
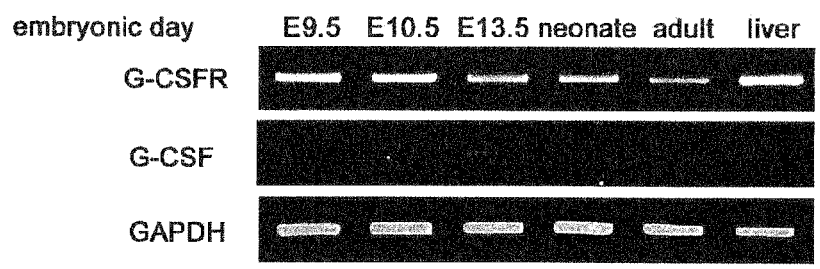
FIG. 3 presents photographs of RT-PCR analysis for the expression of G-CSFR and G-CSF in fetal mouse hearts (at E9.5, E10.5 and E13.5), neonatal mouse hearts, adult mouse hearts and mouse livers. As a control, GAPDH (glyceraldehyde-3-phosphate dehydrogenase) was used.

G-CSFR and G-CSF expression was studied in fetal mouse hearts (at E9.5, E10.5 and E13.5), neonatal mouse hearts, adult mouse hearts and mouse livers. GAPDH (glyceraldehyde-3-phosphate dehydrogenase), which is a gene specific to cardiomyocytes, was used as a control. From each tissue, total RNA was extracted with Trizol reagent (GIBCO) and analyzed by RT-PCR according to the reported method (Niwa, H. et al., Nat. Genet. 24, 372-376 (2000)). The results obtained are shown in FIG. 3. G-CSFR was found to be strongly expressed in the fetal hearts at E9.5 and E10.5.

Example 2

In Vivo Effect of G-CSF on Cardiogenesis (1)

Figure 4:
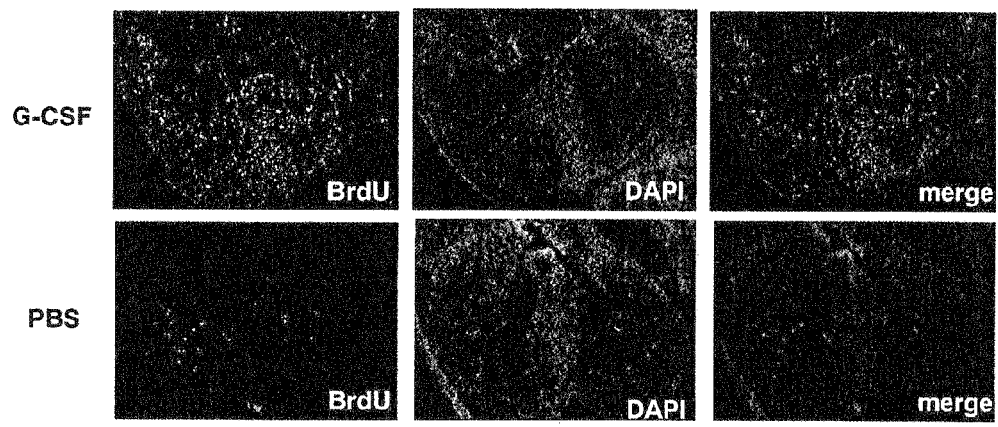
FIG. 4 presents photographs of immunostained fetal heart sections prepared from pregnant mice administered with G-CSF or PBS (phosphate-buffered physiological saline; serving as a control) and then with BrdU (bromodeoxyuridine) by the intraperitoneal route.

At 9.0 days of pregnancy, mice were laparotomized and G-CSF (100 ng/kg) or PBS (phosphate-buffered physiological saline; serving as a control) was directly administered into their uteri. At 9.5 days of pregnancy, the mice were then administered with BrdU (bromodeoxyuridine) by the intraperitoneal route. BrdU is incorporated during DNA synthesis and allows proliferation assessment by immunostaining. At 12.5 days of pregnancy, fetuses were collected to prepare heart sections, which were then analyzed in the same manner as shown for immunostaining in Example 1(2). The results obtained are shown in FIG. 4. It was confirmed that G-CSF promoted fetal myocardial proliferation.

Figure 5:
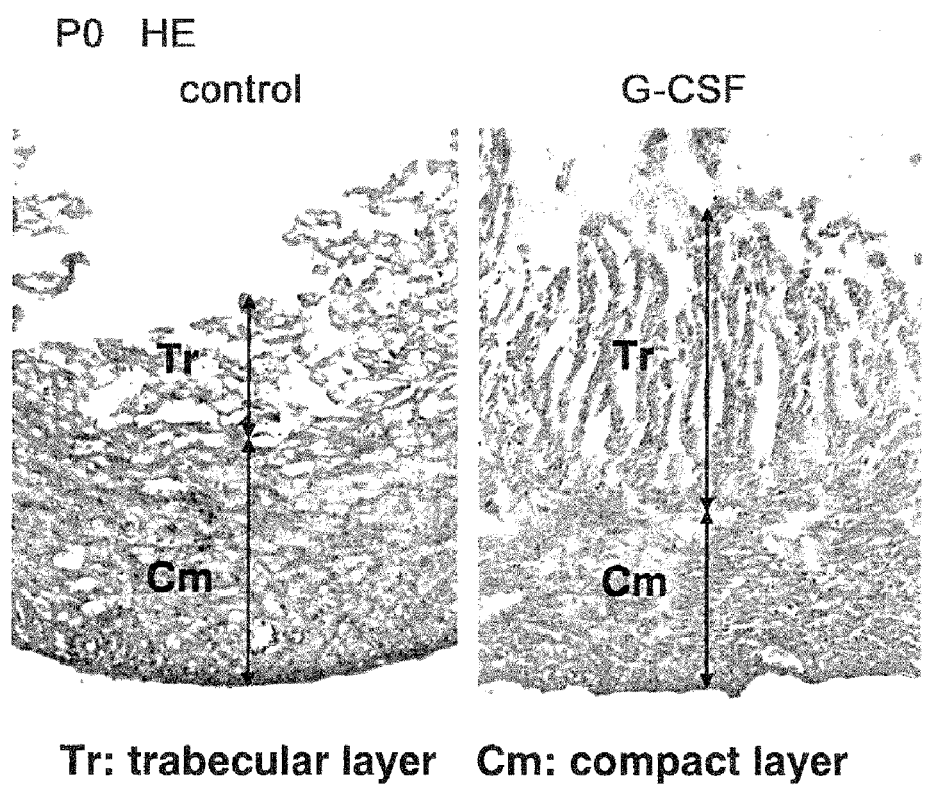
FIG. 5 shows the effect of G-CSF administered to pregnant mice.

In addition, FIG. 5a shows heart sections stained with hematoxylin-eosin and observed under a microscope. The fetal hearts receiving G-CSF administration were found to have an extended trabecular layer.

Further, the same test was also performed on G-CSF receptor-deficient G-CSFR knockout mice (hereinafter referred to as G-CSF$^{-/-}$ mice) (kindly provided by Dr. Daniel C. Link, Washington University, School of Medicine) (Richards et al., Blood, 102, 3562-3568, (2003)) in comparison with wild-type mice. FIG. 5b shows heart sections stained with hematoxylin-eosin and observed under a microscope. In the G-CSF$^{-/-}$ mice, fetal hearts had significantly thinner atrial and ventricular walls when compared to the wild-type mice, and some mice showed atrial septal defect. Approximately 50% of these mice died during the late embryonic stage.

Moreover, for quantification of the myocardial proliferation-promoting effect, the BrdU labeling index was calculated by the following equation. It should be noted that wild-type mice were used in this test, which were administered with BrdU at 10.5 days of pregnancy and analyzed at 12.5 days of pregnancy.

BrdU labeling index=BrdU positive nuclei/total nuclei×100(%)

Figure 6:
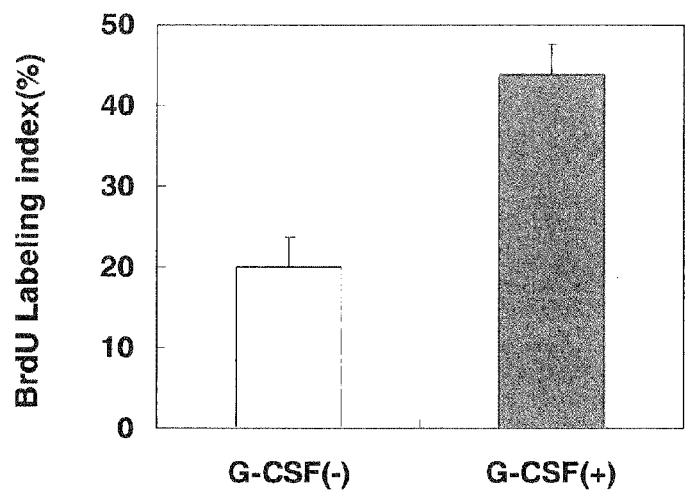
FIG. 6 is a graph showing the BrdU labeling index calculated for each case.

The results obtained are shown in FIG. 6. G-CSF administration was observed to enhance myocardial proliferation.

Example 3

In Vivo Effect of G-CSF on Cardiogenesis (2)

Figure 7:
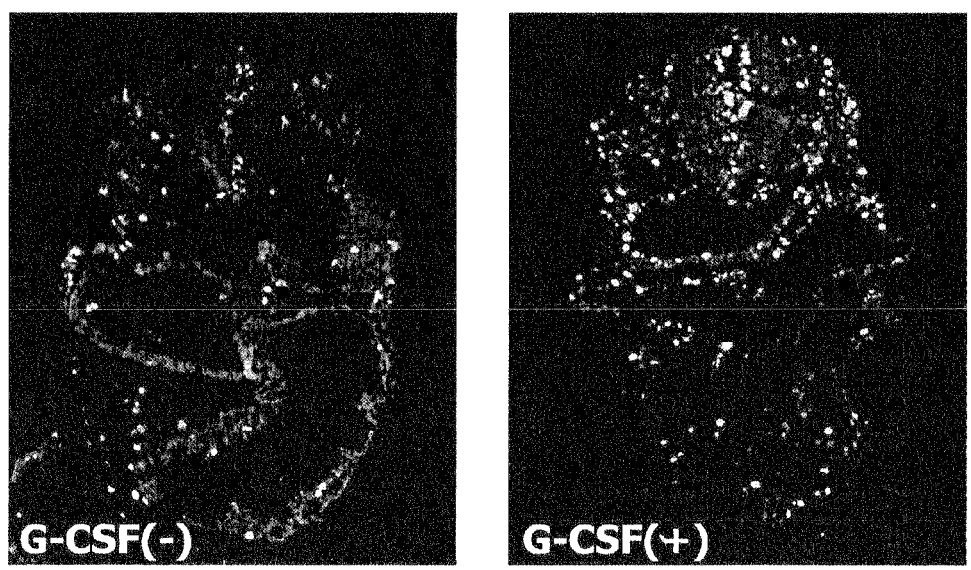
FIG. 7 presents photographs of fetal heart sections immunostained with Phospho-Histon H3, which were prepared from pregnant mice administered with G-CSF.

G-CSF (2 ng) was directly administered into the uteri of pregnant mice at 9.0 days of pregnancy. At 13.5 days of pregnancy, fetuses were collected to prepare heart sections, which were then immunostained with Phospho-Histon H3. Phospho-Histon H3 is a dye that is specifically stained during the cell proliferation process. The results obtained are shown in FIG. 7. G-CSF administration was observed to enhance fetal myocardial proliferation.

Next, the labeling index was calculated by the following equation.

Labeling index=Phospho-Histon H3 positive nuclei/total nuclei×100(%)

Figure 8:
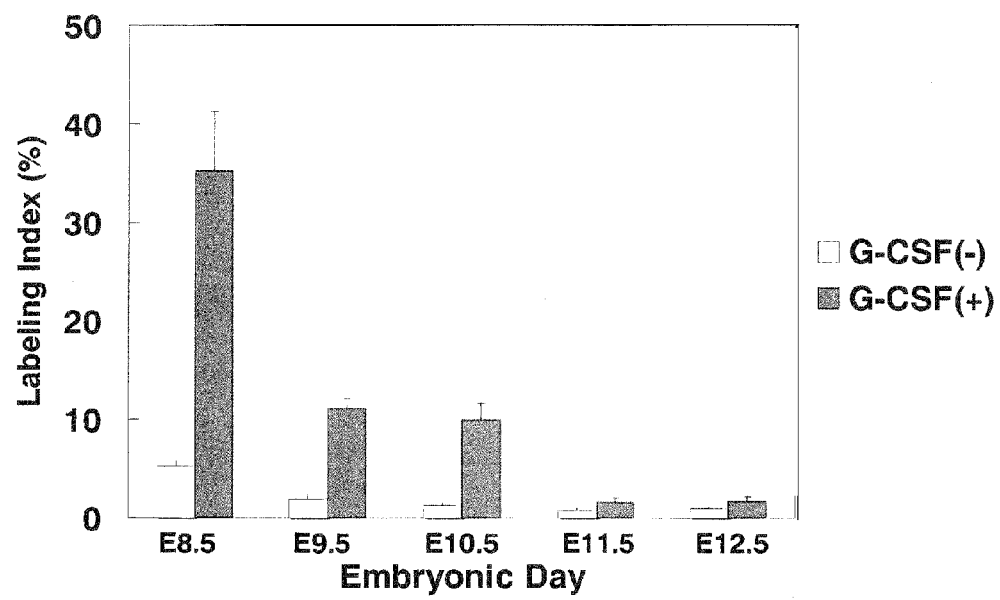
FIG. 8 is a graph showing the Phospho-Histon H3 labeling index calculated for each case.

The results obtained are shown in FIG. 8. G-CSF was observed to strongly enhance myocardial proliferation at embryonic days 8.5 to 10.5.

Figure 9:
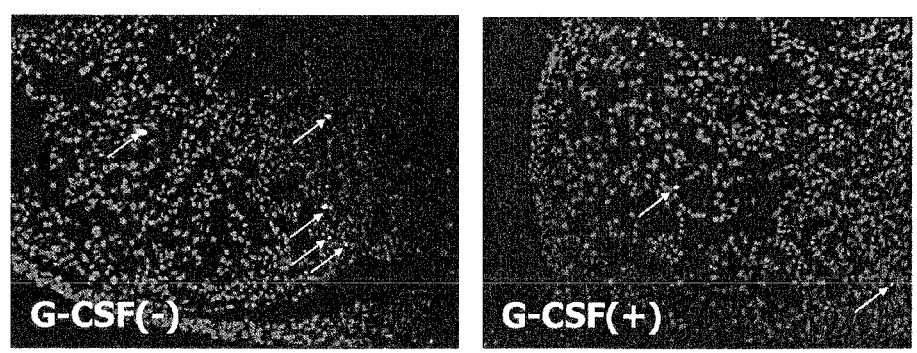
FIG. 9 presents photographs of Tunel-stained hearts at embryonic day 10.5.

Moreover, to study the effect of G-CSF on apoptosis in embryonic hearts, hearts at embryonic day 10.5 were stained with Tunel. Tunel staining is a staining technique by which DNA fragments generated during apoptosis can be distinguished. The results obtained are shown in FIG. 9. The hearts at embryonic day 10.5 showed little apoptosis.

Example 4

Expression of G-CSF Receptor in ES Cell-Derived Cardiomyocytes

In the experiments described below, EB3 cells (kindly provided by Dr. Hitoshi Niwa of Riken, Japan) and R1 cells (kindly provided by Dr. Andrew Nagy of Mount Sinai Hospital, Canada) were used as ES cells. These ES cells were maintained on gelatin-coated plates in Glasgow Minimum Essential Medium (GMEM; Sigma) containing 10% fetal bovine serum, 2 mM L-glutamine, 0.1 mM nonessential amino acid solution, 1 mM sodium pyruvate, 0.1 mM 2-mercaptoethanol and 2000 U/mL leukemia inhibitory factor (LIF) (ESGRO; Chemicon).

Suspension culture was performed as follows to form EBs from ES cells. ES cells were cultured for 3 days on gelatin-coated plates in α-MEM medium containing 10% fetal bovine serum, 2 mM L-glutamine, 0.1 mM nonessential amino acid solution, 1 mM sodium pyruvate, 0.1 mM 2-mercaptoethanol, 2000 U/mL leukemia inhibitory factor and 0.15 µg/ml Noggin (Noggin-Fc, R&D). The ES cells were then dispersed into single cells by treatment with a trypsin solution, and further cultured on uncoated Petri dishes using a three-dimensional culture system in the same differentiation medium as used above (except being free from LIF) to form spheroids, from which EBs (embryoid bodies) were induced. Under these experimental conditions, ES cells will start to aggregate and form EBs immediately after the initiation of suspension culture, and spontaneous beating will be observed in some EBs from about 7 to 8 days after suspension culture.

Figure 10:
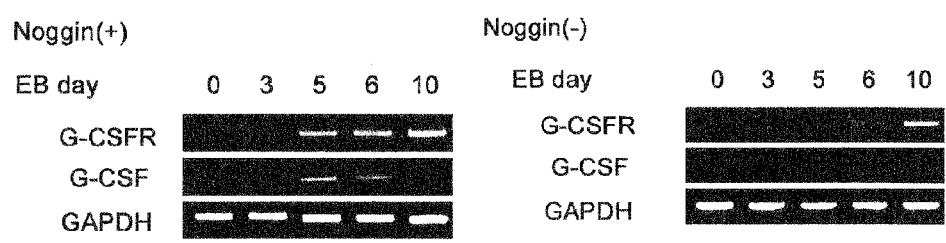
FIG. 10 presents photographs showing the results of RT-PCR analysis for the expression of G-CSFR in EBs derived from ES cells treated with Noggin (Noggin(+) group) and in EBs derived from ES cells not treated with Noggin (Noggin(−) group). GAPDH, which is a gene specific to cardiomyocytes, was used as a control.

The above procedure was used to prepare EBs derived from ES cells treated with Noggin (Noggin(+) group) and EBs derived from ES cells not treated with Noggin (Noggin(−) group), followed by RT-PCR to analyze G-CSFR expression in the EBs. GAPDH, which is a gene specific to cardiomyocytes, was used as a control. The results obtained are shown in FIG. 10. In the EBs derived from ES cells treated with Noggin (Noggin(+) group), G-CSFR expression was observed to start from 5 days after EB formation.

Figure 11:
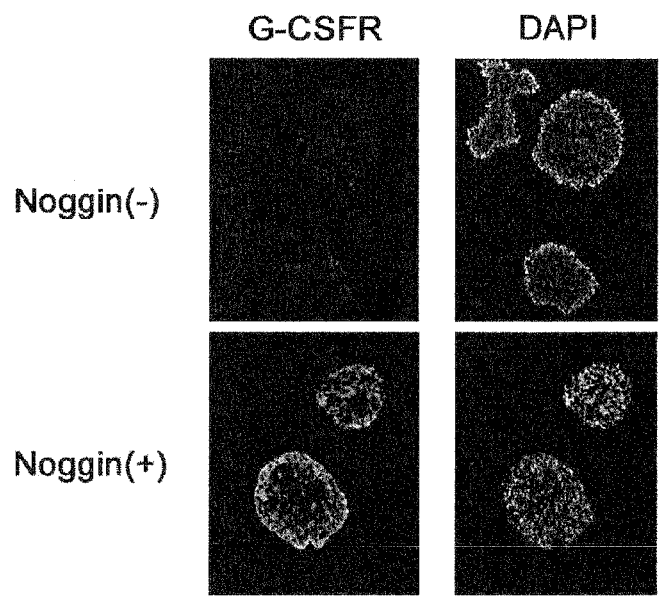
FIG. 11 presents photographs showing the results of immunostaining analysis for the expression of G-CSFR in EBs derived from ES cells treated with Noggin (Noggin(+) group) and in EBs derived from ES cells not treated with Noggin (Noggin(−) group).

In addition, FIG. 11 shows the results of immunostaining using EBs at 6 days after EB formation. In the EBs derived from ES cells treated with Noggin (Noggin(+) group), G-CSFR expression is increased, indicating that Noggin-mediated myocardial induction enhances G-CSFR expression.

Figure 12:
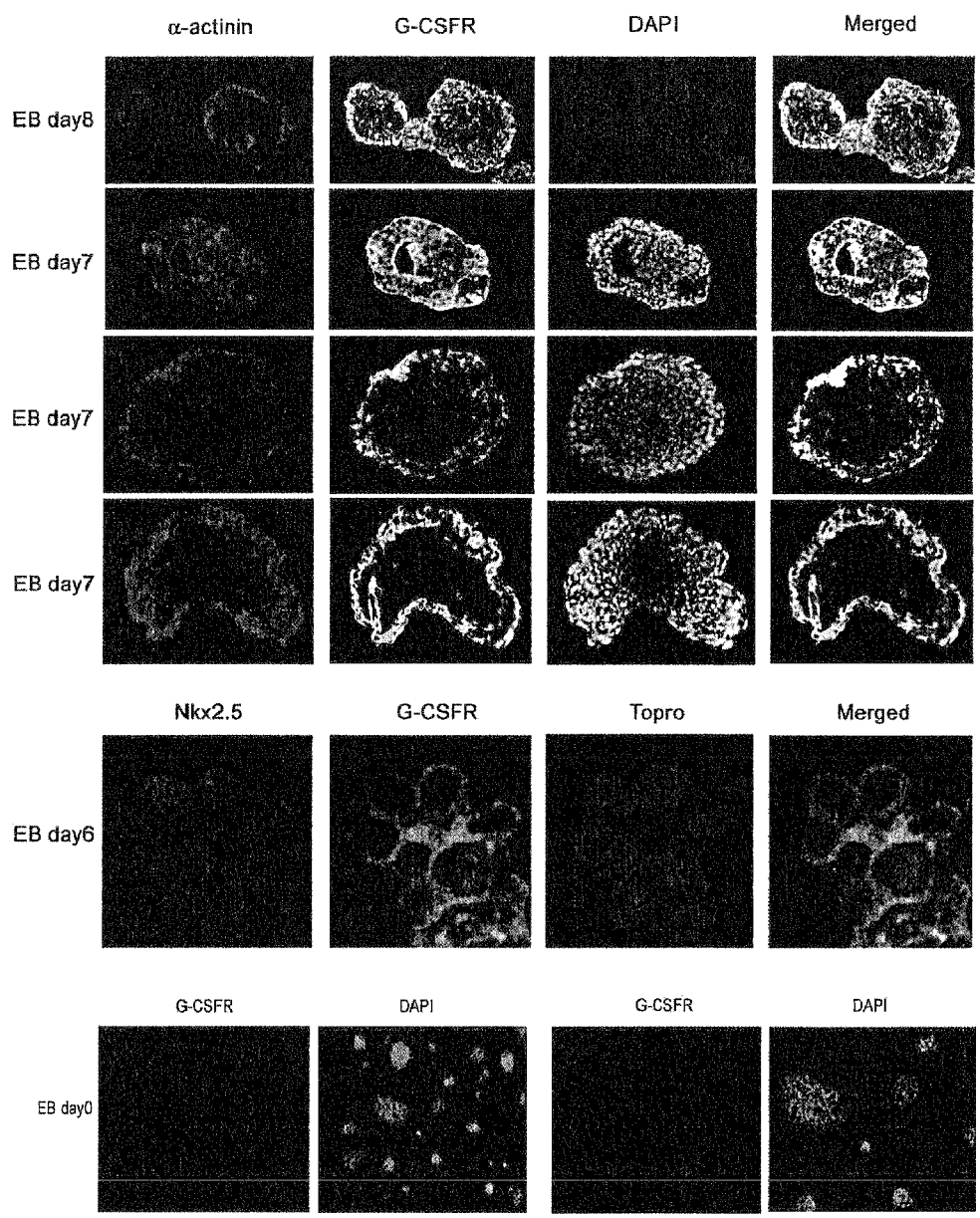
FIG. 12 presents photographs of immunostaining showing the expression of G-CSFR or cardiomyocyte-specific protein α-actinin in EBs at 6, 7 and 8 days after EB formation.

Next, EBs at 6, 7 and 8 days after EB formation were used and immunostained in the same manner as shown in Example 1(2). The results obtained are shown in FIG. 12. These EBs were embedded in OCT to prepare sections, which were then reacted with primary antibodies, i.e., G-CSF receptor antibody (shown above) at a ratio of 1:50 and anti-α-actinin antibody (EA-53, Sigma) at a ratio of 1:800, and further reacted with secondary antibodies, i.e., Alexa488 and Alexa546, followed by nuclear staining. In the EBs at 6, 7 and 8 days after EB formation, cardiomyocyte marker α-actinin and G-CSF were found to be co-expressed, indicating that G-CSF is expressed together with a cardiomyocyte marker when ES cells are induced to differentiate into cardiomyocytes.

Example 5

Differentiation-Inducing Effect of G-CSF on ES Cell-Derived Cardiomyocytes

Figure 13:
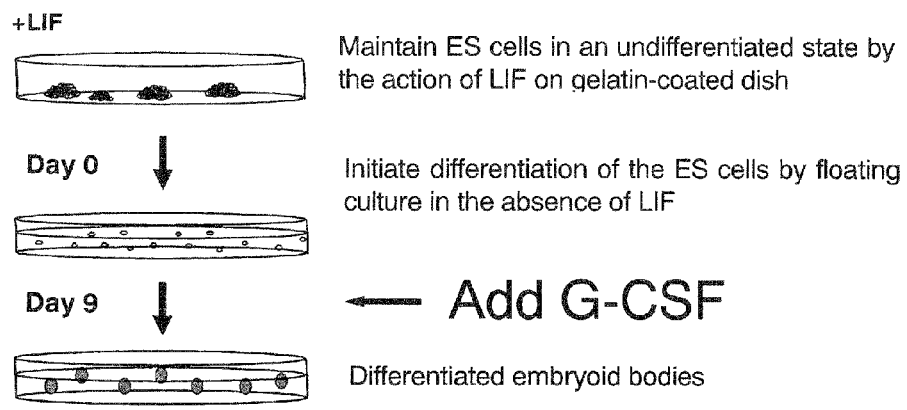
FIG. 13 shows test procedures for G-CSF-mediated induction of cardiomyocyte differentiation.
Figure 14:
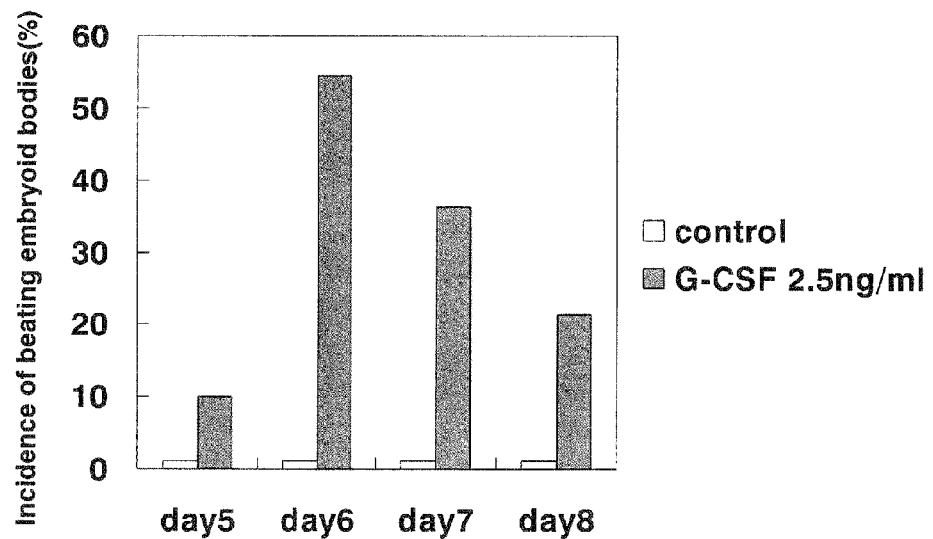
FIG. 14 is a graph showing the optimum timing of G-CSF administration for induction of cardiomyocyte differentiation.

An induction test of cardiomyocyte differentiation was performed using G-CSF according to the procedures shown in FIG. 13. Namely, on gelatin-coated dishes, ES cells were maintained in an undifferentiated state in the presence of LIF, and suspension culture was started at day 0 in the absence of LIF to initiate differentiation of the ES cells, whereby EBs which had differentiated into cardiomyocytes were obtained at day 9. At days 5, 6, 7 and 8, G-CSF (2.5 ng/ml) was added and studied for its effect on EB formation. The results obtained are shown in FIG. 14. This effect was calculated by dividing the number of autonomously beating EBs by the total number of EBs. When administered at day 6, G-CSF showed the greatest effect on EB formation, indicating that the optimum timing of G-CSF administration was day 6.

Figure 15:
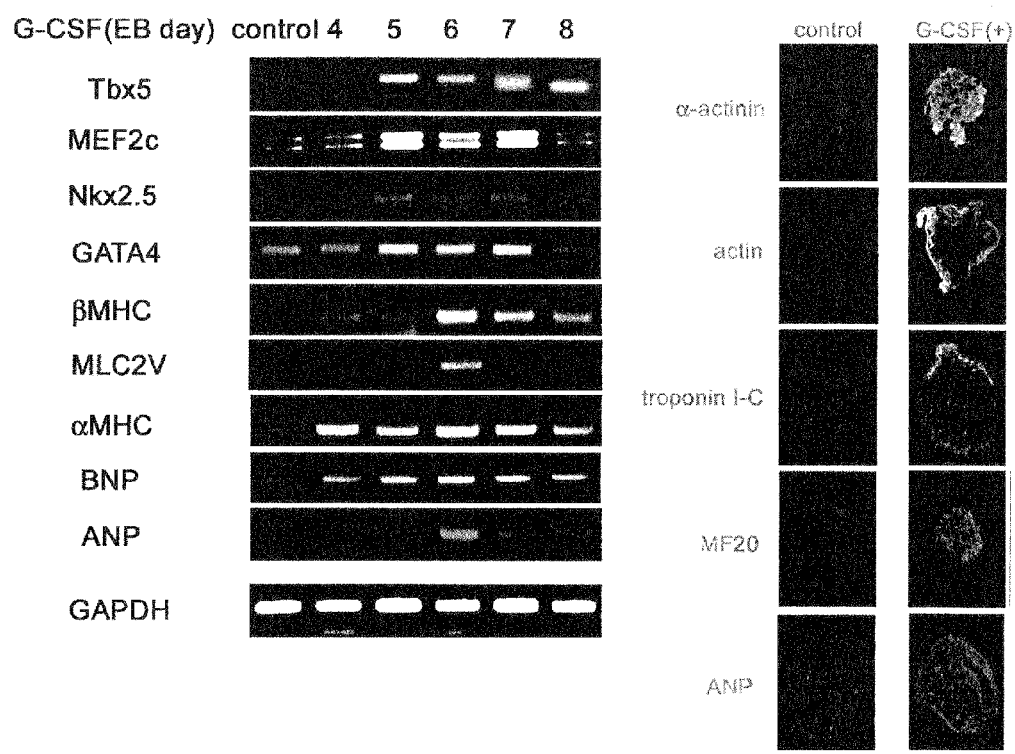
FIG. 15 presents photographs showing the results of RT-PCR and immunostaining analyses for the expression of various cardiomyocyte-specific genes using EBs at 9 days after EB formation.

Next, EBs at day 9 were used and analyzed for the expression of various cardiomyocyte-specific genes by RT-PCR and immunostaining. The cardiomyocyte markers used in RT-PCR were Tbx-5, MEF-2c (muscle enhancement factor-2c), Nkx2.5, GATA-4, βMHC (β myosin heavy chain), MLC-2v (myosin light chain-2v), αMHC (α-myosin heavy chain), BNP (brain natriuretic peptide), ANP (atrial natriuretic peptide) and GAPDH (glyceraldehyde-3-phosphate dehydrogenase). The cardiomyocyte markers used in immunostaining were α-actinin, actin, troponin 1-C, MF20 and ANP. The results obtained are shown in FIG. 15. In the G-CSF-treated group, all the cardiomyocyte markers showed increased expression levels.

Figure 16:
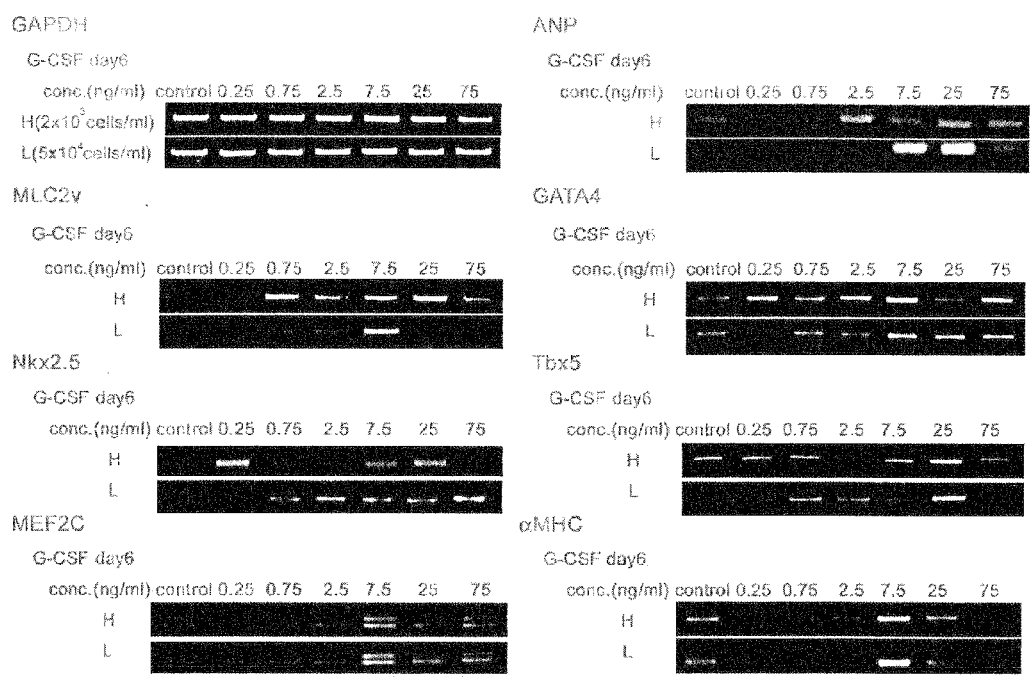
FIG. 16 presents photographs showing the results of RT-PCR analysis for the expression of various cardiomyocyte markers in EBs at day 6 upon G-CSF addition at various concentrations in order to study the optimum concentration of G-CSF.

Further, to study the optimum concentration of G-CSF, G-CSF was added at various concentrations (0.25, 0.75, 2.5, 7.5, 25, 75 ng/ml) to EBs at day 6, followed by RT-PCR to analyze the expression of each cardiomyocyte marker. It should be noted that EBs prepared at two cell densities, H ($2 \times 10^3$ cell/ml) and L ($5 \times 10^4$ cell/ml), were used in this test. The results obtained are shown in FIG. 16. Regardless of the cell density, the contractile proteins, transcription factors and secretory proteins all showed increased expression levels upon G-CSF addition at 0.25 to 25 ng/ml when compared to the control group, suggesting that an optimum concentration lies within this concentration range.

Figure 17:
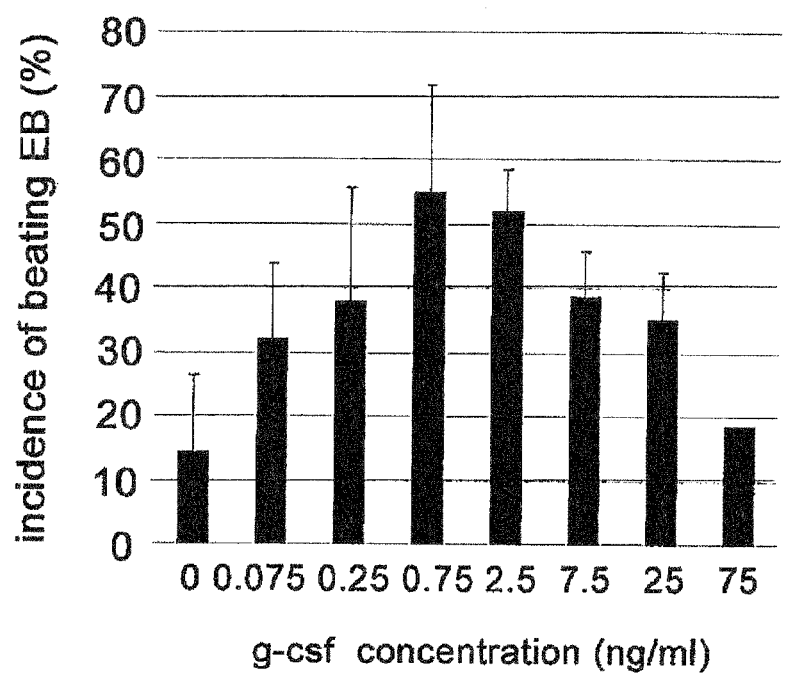
FIG. 17 is a graph showing the optimum concentration of G-CSF for induction of cardiomyocyte differentiation.

Based on the above results, the optimum concentration of G-CSF was determined. The results obtained are shown in FIG. 17. The optimum concentration was studied by comparing the values calculated by dividing the number of autonomously beating EBs by the total number of EBs. As a result, the optimum concentration of G-CSF was found to be 0.75 ng/ml.

Example 6

Figure 18:
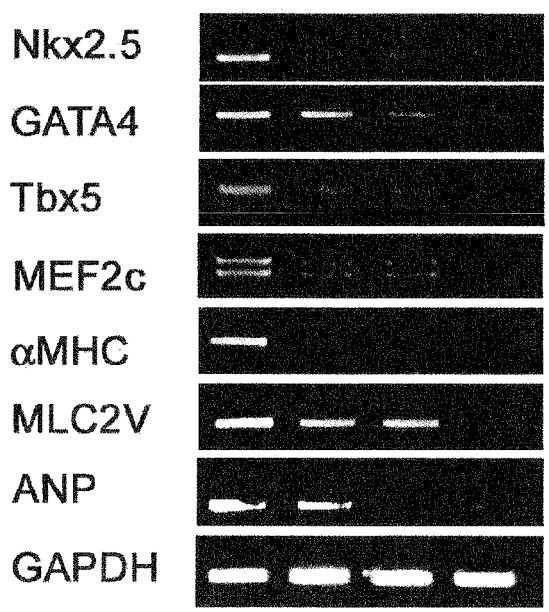
FIG. 18 presents photographs showing the results of RT-PCR analysis for the expression of various cardiomyocyte markers in the presence of anti-G-CSF antibody at various concentrations in order to study the effect of anti-G-CSF antibody against the promoting effect of G-CSF treatment to induce myocardial differentiation from ES cells.

Inhibitory Effect of G-CSF Antibody Against Myocardial Differentiation-Inducing Effect of G-CSF To confirm a possibility that the promoting effect of G-CSF treatment to induce myocardial differentiation from ES cells would be mediated by the endogenous G-CSF signaling pathway, anti-G-CSF antibody (R&D systems) was added to medium simultaneously with G-CSF treatment and studied for its effect. EBs at day 6 were treated with G-CSF (7.5 ng/mL) in the presence of anti-G-CSF antibody at various concentrations (0, 1, 3, 9 ng/ml) to study the effect of anti-G-CSF antibody using various cardiomyocyte markers. The results obtained are shown in FIG. 18. The anti-G-CSF antibody was observed to reduce the expression of the cardiomyocyte markers in a concentration-dependent manner.

Example 7

Proliferation-Promoting Effect of G-CSF on ES Cell-Derived Cardiomyocytes

Figure 19:
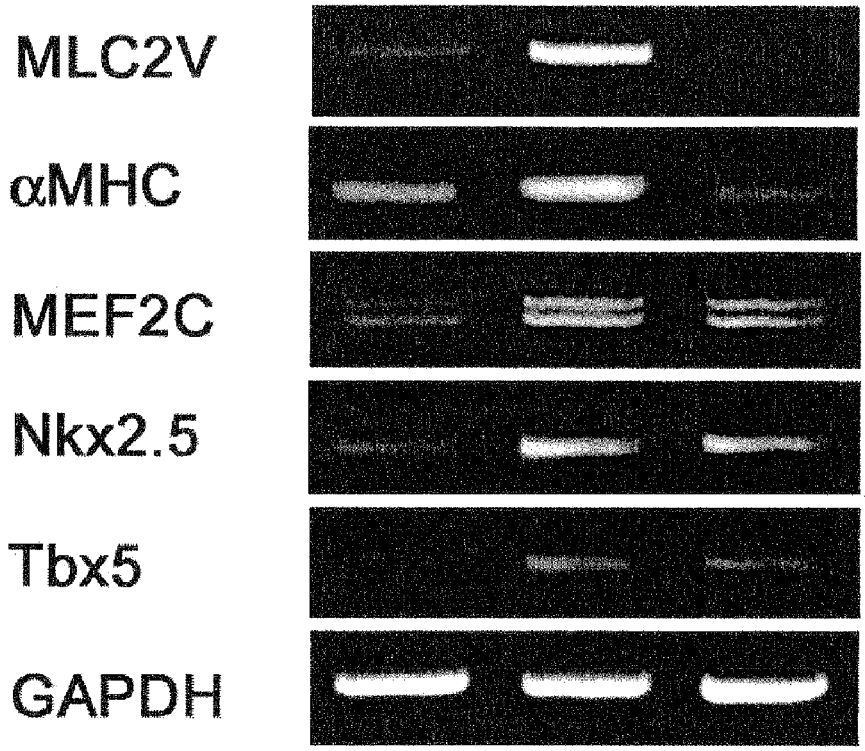
FIG. 19 presents photographs showing the results of RT-PCR analysis for the expression of various cardiomyocyte markers in EBs at day 6 in the G-CSF-treated and untreated groups and in the G-CSF+nocodazole-treated group in order to test the proliferation-promoting effect of G-CSF on ES cell-derived cardiomyocytes.

To test the proliferation-promoting effect of G-CSF on ES cell-derived cardiomyocytes, EBs at day 6 were used to prepare G-CSF (7.5 ng/mL)-treated and untreated groups and a G-CSF+nocodazole (0.2 μg/mL)-treated group. Nocodazole is a drug that specifically inhibits cell division based on its inhibitory effect against spindle fiber formation. These three groups were tested for various cardiomyocyte markers by RT-PCR. The results obtained are shown in FIG. 19. Nocodazole added simultaneously with G-CSF treatment inhibited cell division and hence cancelled the increased expression of the cardiomyocyte markers. This indicates that the effect of G-CSF is to promote proliferation of cardiomyocyte progenitor cells.

Figure 20:
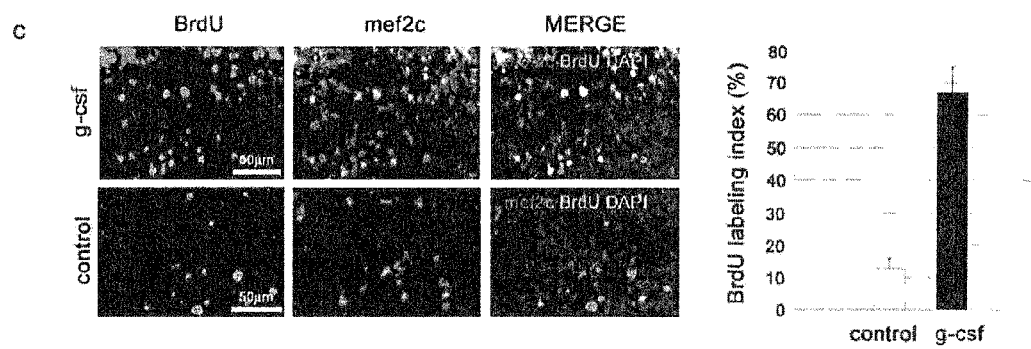
FIG. 20 presents photographs showing the results of double immunostaining with anti-BrdU antibody and anti-mef2c antibody in the G-CSF-treated and untreated groups (left panel) and a graph showing the BrdU labeling index calculated for each group (right panel).

In addition, EBs at day 6 were used to prepare G-CSF (2.5 ng/mL)-treated and untreated groups, which were then incubated with BrdU for 18 hours. FIG. 20 shows the results of double immunostaining with anti-BrdU antibody (Roche) and anti-mef2c antibody (Santa Cruz) in these groups (left panel). FIG. 20 also shows the BrdU labeling index calculated for each group (right panel). G-CSF was confirmed to promote cell proliferation of cardiomyocytes.

Example 8

Effect of G-CSF on Primate Cardiogenesis

Preparation of Common Marmoset ES (CMES) Cells

To test the effect of G-CSF on primate cardiogenesis, common marmoset ES (CMES) cells (#20) (Sasaki et al., Stem Cells 23, 1304-1313 (2005)) were used. CMES cells were maintained on a layer of mitotically inactivated mouse embryonic fibroblasts (MEFs) in Knockout DMEM (GIBCO) medium supplemented with 20% Knockout Serum Replacement (KSR; GIBCO), 1 mM L-glutamine (GIBCO), 0.1 mM MEM nonessential amino acids (GIBCO), 0.1 mM β-mercaptoethanol (2-ME; Sigma), 10 ng/ml fibroblast growth factor (bFGF; Invitrogen) and 10 ng/ml human leukemia inhibitory factor (hLIF; Alomone labs). CMES cells were passaged every 5 days to maintain their undifferentiated state.

Preparation of EBs

Undifferentiated CMES cells were removed from the MEF feeder layer, dissociated into small colonies with a dissociation solution for human and monkey ES cells (ReproCELL. JAPAN), and then cultured to form EBs in suspension culture using HydroCell culture plates (CellSeed, JAPAN) in medium free from bFGF and hLIF.

Study of G-CSF Effect

Figure 21:
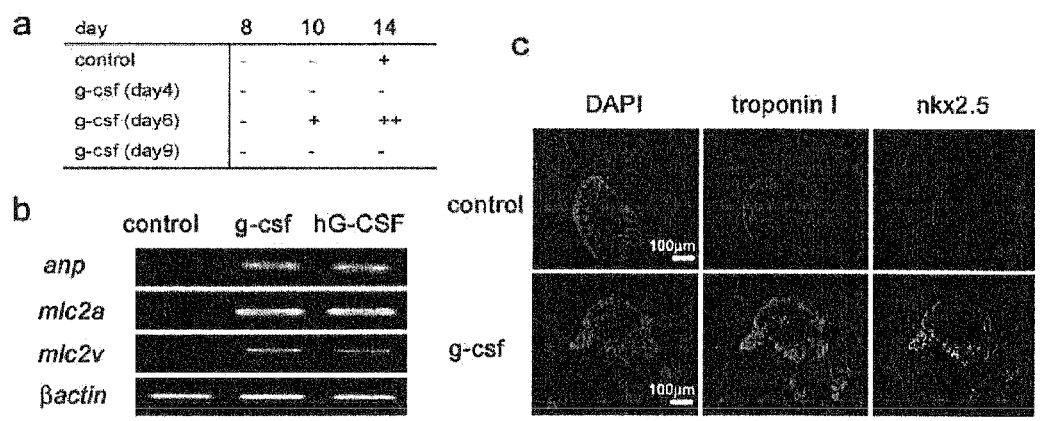
FIG. 21 shows the effect of G-CSF on common marmoset ES (CMES) cells.

At 4, 6 and 9 days after EB formation, G-CSF (2.5 ng/mL) was added to observe spontaneous beating. The results obtained are shown in FIG. 21a. The best result was obtained upon addition at 6 days after EB formation, and the difference between G-CSF-treated and untreated groups became evident at 14 days after EB formation. The effect of G-CSF addition on cardiogenesis was observed to be highest at 6 days after EB formation and lower at either earlier or later stages.

FIG. 21b shows the results of RT-PCR analysis for the expression of various cardiomyocyte markers in CMES cells treated with mouse G-CSF or human G-CSF. Both mouse G-CSF and human G-CSF were observed to strongly enhance the expression of the cardiomyocyte markers. FIG. 21c shows the results of immunostaining. G-CSF enhanced cardiac troponin I- and Nkx2.5-positive areas in CMES-derived EBs.

These results indicated that G-CSF was essential for primate cardiomyocyte proliferation, and thus suggested the role of G-CSF in all mammals, including humans.

The invention claimed is:

1. A method for inducing differentiation of ES cells into cardiomyocytes in vitro, which comprises culturing the ES cells in the presence of an agonist for G-CSF receptor, wherein the agonist for G-CSF receptor is added to the cell culture solution 5 to 8 days after removal of leukemia inhibitory factor (LIF) from the culture medium.

2. The method according to claim 1, wherein the agonist for G-CSF receptor is G-CSF.

3. The method according to claim 2, which comprises the following steps:
   (a) culturing the ES cells;
   (b) adding the G-CSF to a cell culture solution; and
   (c) culturing the ES cells using the culture solution from step (b).

4. The method according to claim 1, which further comprises the step of culturing the ES cells in the presence of a substance that inhibits BMP signaling, prior to culturing the ES cells in the presence of the agonist for G-CSF receptor.

5. The method according to claim 4, wherein the substance that inhibits BMP signaling is Noggin.

6. A method for producing cardiomyocytes in vitro, which comprises culturing ES cells in the presence of an agonist for G-CSF receptor, wherein the agonist for G-CSF receptor is added to the cell culture solution 5 to 8 days after removal of leukemia inhibitory factor (LIF) from the culture medium.

7. The method according to claim 6, wherein the agonist for G-CSF receptor is G-CSF.

8. The method according to claim 6, which comprises the following steps:
   (a) culturing the ES cells;
   (b) adding the G-CSF to the cell culture solution at the $5^{th}$ to $8^{th}$ day after removal of LIF from the culture medium; and
   (c) culturing the ES cells using the culture solution from step (b).

9. The method according to claim 6, which further comprises the step of culturing the ES cells in the presence of a substance that inhibits BMP signaling, prior to culturing the ES cells in the presence of the agonist for G-CSF receptor.

10. The method according to claim 9, wherein the substance that inhibits BMP signaling is Noggin.

11. The method according to claim 4, wherein the agonist for G-CSF receptor is G-CSF.

* * * * *

SEQUENCE LISTING

<160> NUMBER OF SEQ ID NOS: 5

<210> SEQ ID NO 1
<211> LENGTH: 174
<212> TYPE: PRT
<213> ORGANISM: Homo sapiens

<400> SEQUENCE: 1

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 2
<211> LENGTH: 22
<212> TYPE: DNA
<213> ORGANISM: Artificial
<220> FEATURE:
<223> OTHER INFORMATION: Sense primer for amplifying human G-CSF receptor.

<400> SEQUENCE: 2
cccctcaaac ctatcctgcc tc                                              22

```
<210> SEQ ID NO 3
<211> LENGTH: 22
<212> TYPE: DNA
<213> ORGANISM: Artificial
<220> FEATURE:
<223> OTHER INFORMATION: Antisense primer for amplifying human G-CSF
      receptor.

<400> SEQUENCE: 3
tccaggcaga gatcagcgaa tg                                              22

<210> SEQ ID NO 4
<211> LENGTH: 20
<212> TYPE: DNA
<213> ORGANISM: Artificial
<220> FEATURE:
<223> OTHER INFORMATION: Sense primer for amplifying Nkx2.5.

<400> SEQUENCE: 4
cagtggagct ggacaaagcc                                                 20

<210> SEQ ID NO 5
<211> LENGTH: 20
<212> TYPE: DNA
<213> ORGANISM: Artificial
<220> FEATURE:
<223> OTHER INFORMATION: Antisense primer for amplifying Nkx2.5.

<400> SEQUENCE: 5
tagcgacggt tctggaacca                                                 20
```